United States Patent [19]

Archer et al.

[11] 4,087,546

[45] May 2, 1978

[54] HEXAHYDRO-DIBENZO[b,d]PYRAN-9-ONES AS ANTIASTHMATIC DRUGS

[75] Inventors: Robert A. Archer; Louis Lemberger, both of Indianapolis, Ind.

[73] Assignee: Eli Lilly and Company, Indianapolis, Ind.

[21] Appl. No.: 658,438

[22] Filed: Feb. 17, 1976

[51] Int. Cl.$^2$ .................... A01N 9/28; A61K 31/35
[52] U.S. Cl. ................................ 424/283; 424/32
[58] Field of Search .............................. 424/283

[56] References Cited

U.S. PATENT DOCUMENTS

| | | | |
|---|---|---|---|
| 3,928,598 | 12/1975 | Archer | 424/283 |
| 3,953,603 | 4/1976 | Archer | 424/283 |
| 3,968,125 | 7/1976 | Archer | 424/283 |
| 3,987,188 | 10/1976 | Archer | 424/283 |

Primary Examiner—Dale R. Ore
Attorney, Agent, or Firm—James L. Rowe; Everet F. Smith

[57] ABSTRACT

Use of 1-hydroxy-3-alkyl-6,6a,7,8,10,10a-hexahydro-9H-dibenzo[b,d]pyran-9-ones as antiasthmatic drugs.

7 Claims, No Drawings

Illustrative of R' in Formula IV when it is $C_7$–$C_{10}$ normal alkyl are n-heptyl, n-octyl, n-nonyl and n-decyl. Illustrative groups which R" can represent in the grouping

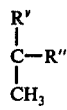

are the following: ethyl, n-propyl, isopropyl, sec-butyl, n-butyl, isobutyl, iso-amyl, t-amyl, n-amyl 2-pentyl, 3-pentyl, 3-methyl-2-butyl, 2-hexyl, 1-hexyl, 3-hexyl, 4-methyl-1-pentyl, 3-methyl-1-pentyl, 3-methyl-2-pentyl, neopentyl, 3,3-dimethyl-1-butyl, 3,3-dimethyl-1-pentyl and the like groups. Thus groups illustrative of R', when it is the above moiety are the following: 1,2-dimethylheptyl, 1,1-dimethylheptyl, 1,2-dimethylhexyl, 1,1-dimethylpentyl, 1,1-dimethylpropyl, 1-methylbutyl, 1-methyloctyl, 1-methylheptyl, 1-methylhexyl and the like. The term $C_1$–$C_4$ alkanoyl which R'" can represent includes acetyl, propionyl, n-butyryl and isobutyryl.

The following hexahydrodibenzopyranones illustrate the scope of Formula IV above for compounds useful in the processes and compositions of this invention.

1-Acetoxy-3-n-heptyl-6,6a,7,8,10,10a-hexahydro-9H-dibenzo[b,d]pyran-9-one, 1-hydroxy-3-(1'-methyl-2'-butenyl)-6,6-dimethyl-6,6a,7,8,10,10a-hexahydro-9H-dibenzo[b,d]pyran-9-one, 1-propionoxy-3-(1'-methylheptyl)-6,6-dimethyl-6,6a,7,8,10,10a-hexahydro-9H-dibenzo[b,d]pyran-9-one, 1-hydroxy-3-(1',1'-dimethylheptyl)-6,6a,7,8,10,10a-hexahydro-9H-dibenzo[b,d]pyran-9-one, 1-butyroxy-3-(1',2'-dimethylpentyl)-6,6-dimethyl-6,6a,7,8,10,10a-hexahydro-9H-dibenzo[b,d]pyran-9-one, 1-hydroxy-3-(1',1'-dimethyl-2'-butyl)-6,6a,7,8,10,10a-hexahydro-9H-dibenzo[b,d]pyran-9-one, 1-hydroxy-3-n-heptyl-6,6-dimethyl-6,6a,7,8,10,10a-hexahydro-9H-dibenzo[b,d]pyran-9-one, 1-hydroxy-3-(1',1'-dimethylhexyl)-6,6-dimethyl-6,6a,7,8,10,10a-hexahydro-9H-dibenzo[b,d]pyran-9-one, 1-acetoxy-3-n-heptyl-6,6a,7,8,10,10a-hexahydro-9H-dibenzo[b,d]pyran-9-one, 1-hydroxy-3-(1'-methyl-2'-butyl)-6,6-dimethyl-6,6a,7,8,10,10a-hexahydro-9H-dibenzo[b,d]pyran-9-one, 1-propionoxy-3-(1'-methylheptyl)-6,6-dimethyl-6,6a,7,8,10,10a-hexahydro-9H-dibenzo[b,d]pyran-9-one, 1-hydroxy-3-(1',1'-dimethylhexyl)-6,6a, 7,8,10,10a-hexahydro-9H-dibenzo[b,d]pyran-9-one, 1-n-butyroxy-3-(1',1'-dimethylpentyl)-6,6-dimethyl-6,6a,7,8,10,10a-hexahydro-9H-dibenzo[b,d]pyran-9-one, and 1-acetoxy-3-(1',1'-dimethyl-2'-butyl)-6,6-dimethyl-6,6a,7,8,10,10a-hexahydro-9H-dibenzo[b,d]pyran-9-one, The compounds of this invention in which both R groups in the 6-position of Formula IV are methyl are prepared according to the procedure of Fahrenholtz et al referred to above. In this procedure, an alkyl resorcinol is condensed with a dialkyl α-acetoglutarate followed by cyclization with sodium hydride in DMSO to yield a compound according to Formula I above which, after initial formation and reaction with a Grignard Reagent followed by treatment with 6N acid, yields a 10,10a-dehydro-9H-dibenzo[b,d]pyran of Formula II above. Reduction of the $\Delta^{10(10a)}$ double bond then yields dimethyl compounds according to Formula III.

Compounds in which both R groups attached to $C_6$ are hydrogen in Formula IV are prepared according to the following general procedure: The ketone group of a ketolactone according to Formula I above is reacted with ethylene glycol to form the corresponding 9-ketal. Reduction of the ketal with sodium bismethoxyethoxyaluminum hydride in benzene yields a 2-(2'-hydroxymethyl-5'-ethylenedioxy-$\Delta^1$-cyclohexenyl)-5-alkyl resorcinol of formula V.

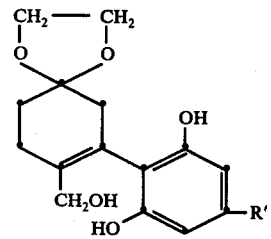

On work-up in acidic medium, the ketal protecting group is removed and a compound of Va is actually isolated.

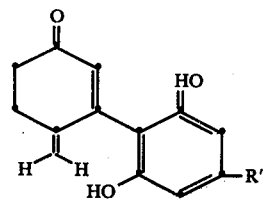

Treatment of this resorcinol (Va) with aluminum oxide in benzene cyclizes the compound to yield a derivative which, upon hydrogenation by the procedures of U.S. Pat. No. 3,507,885—either lithium, sodium, or potassium in liquid ammonia or hydrogenation over Raney nickel at a hydrogen pressure in the range 100–5000 psi—yields a dibenzo[b,d]pyran-9-one according to Formula III above in which both R groups attached to $C_6$ are hydrogen.

Compounds according to formula IV above contain asymmetric centers at 6a and 10a. In addition, there may be asymmetric centers in the side-chain alkyl group as, for example, when R' is 1,2-dimethyl heptyl, two asymmetric centers are present in this side-chain. The Fahrenholtz synthetic procedure described above in which the double bond isomerizes from the $\Delta^{6a(10a)}$ position to the $\Delta^{10(10a)}$ position produces a racemate in which $C_{6a}$ is asymmetric, the hydrogen being either above or below the plane of the dibenzo-pyran fused-ring system. Hydrogenation of the $\Delta^{10(10a)}$ double bond with, for example, an active metal in liquid ammonia produces a second asymmetric center at $C_{10a}$, but the hydrogen which adds to this carbon under the hydrogenation or reduction conditions will usually take the more favorable trans configuration relative to the hydrogen at $C_{6a}$ with a lesser quantity of compound of the cis configuration being produced. Thus, synthesis of a compound in which the side chain contains no asymmetric centers, as for example 1-hydroxy-3-(1',1'-dimethylheptyl)-6,6-dimethyl-6,6a,7,8,10,10a-hexahydro-9H-dibenzo[b,d]-pyran-9-one, will result in two racemates or racemic pairs in which the trans racemate - predominates. Compounds such as 1-hydroxy-3-(1',2'-dimethylheptyl-6,6-dimethyl-6,6a,7,8,10,10a-hexahydro-9H-dibenzo[b,d]-pyran-9-one containing two asymmetric centers in the side chain will have a total of four asymmetric centers,

HEXAHYDRO-DIBENZO[B,D]PYRAN-9-ONES AS ANTIASTHMATIC DRUGS

BACKGROUND OF THE INVENTION

1-Hydroxy-9-keto-3-alkyl-7,8,9,10-tetrahydro-6H-dibenzo[b,d]pyrans (preferably named as 1-hydroxy-3-alkyl-6,6a,7,8,10,10a-hexahydro-9H-dibenzo[b,d]pyran-9-ones) were synthesized as intermediates by Fahrenholtz, Lurie and Kierstead, *J. Am. Chem. Soc.*, 88, 2079 (1966), 89 5934 (1967) according to the following reaction procedure: a 5-alkyl resorcinol is reacted with diethyl α-acetylglutarate to form an ethyl 4-methyl-5-hydroxy-7-alkylcoumarin-3-propionate. Cyclization of this lactone ester with a metal hydride yields a tricyclic keto lactone of the following structure (Formula I):

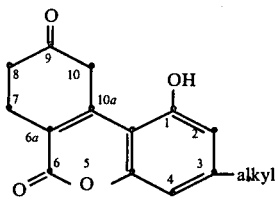

Protection of the 9-keto group by ketal formation followed by treatment of the ketal with a methyl Grignard Reagent and subsequent cyclization and removal of the ketal group yields a 1-hydroxy-3-alkyl-6,6-dimethyl-6,6a,7,8-tetrahydro-9H-dibenzo[b,d]pyran-9-one of Formula II below:

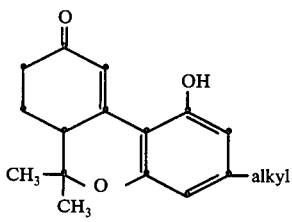

Reduction of the $\Delta^{10(10a)}$ double bond with lithium in liquid ammonia at $-78°$ C. yields predominantly the trans ketone, dl-trans-1-hydroxy-3-alkyl-6,6-dimethyl-6,6a,7,8,10,10a-hexahydro-9H-dibenzo[b,d]pyran-9-one, Formula III, along with minor quantities of the corresponding 6a,10a cis isomer.

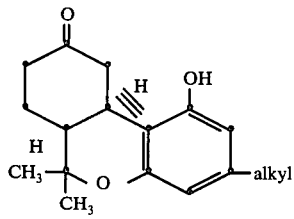

No pharmacological activity was reported for this compound and it was used only as an intermediate. Compounds according to Formula III can readily be transformed by treatment with a methyl Grignard Reagent to the corresponding 9-methyl-9-hydroxy compound, dehydration of which yields directly either a $\Delta^8$ or $\Delta^9$-tetrahydrocannabinol derivative, the latter being an active constituent of hashish. The Fahrenholtz et al synthesis is also described in U.S. Pat. No. 3,507,885 and in U.S. Pat. No. 3,636,058, a continuation-in-part of the previous patent. (In the Fahrenholtz et al patents, structure VI corresponds to Formula I above, structure VII to Formula II above, and structure III to Formula III above). Although apparently only a single compound of Formula III above was actually prepared by Fahrenholtz (the 3-n-pentyl derivative — see example 8 of U.S. Pat. No. 3,636,058), a large number of alkyl substituted resorcinols are described, all of which can be used to synthesize other 3-alkyl derivatives of Formula III. Resorcinols named include 5-(1,2-dimethylheptyl)resorcinol, 5-(1-methyloctyl)resorcinol, 5-(1-methylheptyl)resorcinol, 5-(1,2-dimethylbutyl)resorcinol, etc. Petrzilka, U.S. Pat. No. 3,873,576 covers a different synthetic procedure for preparing $\Delta^9$-T.M.C. which avoids the Fahrenholtz ketone 9-ketone intermediates. A review article, "*Problems of Drug Dependence - Cannabis* (Marijuana), Selected Bibliography (1950–1967) prepared by the Medical Literature Branch, Bureau of Medicine, FDA, Department of Health, Education and Welfare, *Addendum I, Substances Occurring Naturally in Marijuana, etc.,* Isbel, (Washington, D.C., 1968)" and an article entitled *Recent Advances in the Chemistry of Hashish*, Mechoulam and Gaoni, *Fortschritte Der Chemie Organicher Naturstoffe*, 25, 175 (Springer, Wien, 1957) all mention the Fahrenholtz, et al synthesis as well as other synthetic procedures for preparing active tetrahydrocannabinols; no pharmacological activity for compounds having a ketone group at 9 in the dibenzopyran ring system is recorded therein.

Archer U.S. Pat. No. 3,928,598, discloses the use of compounds of Formula IV below as analgesic, sedative antiauxiety and anti-depressant agents.

SUMMARY OF THE INVENTION

This invention provides a process for the treatment of asthma of mammals which comprises administrating to an asthmatic mammal an effective antiasthmatic dose of a compound of Formula IV:

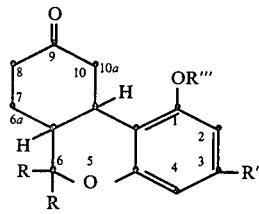

wherein R' is either $C_7$–$C_{10}$ normal alkyl or is

wherein R" is $C_2$–$C_7$ alkyl, $R^v$ is H or methyl, R''' is hydrogen or $C_1$–$C_4$ alkanoyl, and wherein both R groups are the same and can be hydrogen or methyl. Pharmaceutical compositions in unit dosage form for treatment of asthma consisting of a pharmaceutical carrier and, as a therapeutic agent, from 0.1 to 25 mg. of a compound of Formula IV are also described herein. The dosage form may be given one to six times daily, yielding a daily dosage in the range of 0.1 to 100 mgs. of a compound of structure IV with the preferred daily dosage being in the range 1–20 mg.

those at 6a, 10a and at $C_1$- and $C_2$- in the side chain, yielding altogether 16 possible isomers occuring as 8 racemates.

The resorcinol starting materials useful in the Fahrenholtz synthesis such as n-pentyl resorcinol are readily available from the art. Resorcinols with a doubly branched alkyl group in the 5-position can be prepared by the procedure of Adams et al., *J. Am. Chem. Soc.*, 70, 664 (1948). These α,α-branched 5-alkylresorcinols are in general produced by doubly alkylating a 3,5-dimethoxyphenylacetonitrile, converting the nitrile group to a ketone, reducing the ketone carbonyl to an alcohol, dehydrating the alcohol and then hydrogenating the resulting double bond. Demethylation then yields a 5-(1',1'-dimethylalkyl)resorcinol. Resorcinols having an alkyl side chain with an α,β-substitution pattern are in general prepared from 3,5-dimethoxybenzamide. Conversion of the benzamide to a ketone using the appropriate Grignard Reagent followed by the action of a methyl Grignard Reagent on the resulting ketone yields a tertiary carbinol. Dehydration of the carbinol produces an ethylenic compound which on hydrogenation yields a 3,5-dimethoxy-(α,β-substituted alkyl)benzene. This latter compound is readily demethylated to form the corresponding 5-(1'-methyl-2'-alkyl-substituted alkyl)resorcinol. 5-alkyl resorcinols lacking an α branch can be prepared by standard methods available in the art, including the reaction of a nitrile with a Grignard Reagent followed by reduction of the resulting carbonyl, dehydration of the thus formed benzylic alcohol and hydrogenation to yield an alkyl group, or by hydrogenolysis of a benzylic alcohol directly.

The synthesis procedure used for preparing compounds useful in the processes and compositions of this invention is illustrated by the following specific example:

EXAMPLE 1

Preparation of 1-hydroxy-3-(1',1'-dimethylheptyl)-6,6-dimethyl-6,6-dimethyl-6,6a,7,8,10,10a-hexahydro-9H-dibenzo[b,d]pyran-9-one.

A mixture containing 114 g. of 5-(1',1'-dimethylheptyl)resorcinol, 112 g. of diethyl 2-acetylglutarate and 74 g. of phosphorous oxychloride was stirred at ambient temperature for about 10 days. The reaction mixture was then dissolved in ethyl acetate and the ethyl acetate layer washed several times with an equal volume of water until the water wash was neutral to litmus. The organic layer was separated and dried, and the solvent removed by evaporation in vacuo. The residue, comprising ethyl 7-(1',1'-dimethylheptyl)-5-hydroxy-4-methyl-2-oxy-2H-1-benzopyran-3-propionate formed in the above reaction, was purified by chromatography over 2 kg. of neutral alumina using chloroform as the eluant. 142 g. of purified product thus obtained, were dissolved in 300 ml. of DMSO (dimethylsulfoxide), and the solution added in dropwise fashion to a suspension of 33.6 g. of sodium hydride in 100 ml. of DMSO. After the addition had been completed, the reaction mixture was allowed to stand at ambient temperature overnight. Excess sodium hydride present was decomposed by the dropwise addition of ethanol. The reaction mixture was next carefully poured over a mixture of ice and 12 N aqueous hydrochloric acid. A solid resulted comprising 3-(1',1'-dimethylheptyl)-7,10-dihydro-1-hydroxy-6H-dibenzo[b,d]pyran-6,9(8H)-dione, which was collected by filtration. The solid filter cake was dissolved in methyl ethyl ketone and the resulting solution washed with 5 percent aqueous sodium bicarbonate followed by saturated aqueous sodium chloride. The organic layer was dried, and the solvent removed by evaporation in vacuo. Trituration of the crude residue with anhydrous ether followed by filtration (the filtrate being discarded) yielded about 92.6 g. of a light yellow solid. 3-(1',1'-Dimethylheptyl)-7,10-dihydro-1-hydroxy-6H-dibenzo[b,d]pyran-6,9(8H)-dione thus obtained was used in its semipurified state. A solution of 2.3 g. of the above product in 125 ml. of benzene also containing 2.5 ml. of ethylene glycol and 5 mg. of p-toluenesulfonic acid was heated overnight under reflux using a water collector. After cooling, the reaction mixture was poured into 5 percent aqueous sodium bicarbonate. The organic layer was separated, washed with water and then dried. Removal of the organic solvent in vacuo yielded 2.5 g. of 3-(1,',1'-dimethylheptyl)-7,8-dihydro-1-hydroxyspiro-[9H-dibenzo[b,d]pyran-9,2'-[1,3]-dioxolan]-6(10H)-one. This product was also used without purification.

A solution of the product in 50 ml. of anhydrous ether was added dropwise to 46 ml. of a 2.8 M methyl Grignard Reagent in anhydrous ether. After the addition had been completed, the reaction mixture was refluxed overnight, cooled, and then carefully poured into an ice and 6N aqueous hydrochloric acid mixture. Evaporation of the ether by heating on a steam bath yielded a light yellow precipitate which was collected by filtration. The solid material was washed several times with ether to give 1.64 g. of a light yellow solid comprising dl-3-(1',1'-dimethylheptyl)-6,6a,7,8-tetrahydro-1-hydroxy-6,6-dimethyl-9H-dibenzo[b,d]-pyran-9-one; MP = 194°-6° C.

Rf=0.26 (silica gel, 20% ethyl acetate:benzene): UV (ethanol) $\lambda_{max}$ 207/230/323 mμ (ε=25,600/13,200/23,200); IR(Chloroform) 6.1μ (C=O); NMR (CDCl$_3$) δ7.4 (d/J=2 cps/1H/H$_{10}$), δ6.46/6.26(2d/J=2 cps/2H/H$_2$ and H$_4$), δ1.21 (s/6H/gem dimethyl at C-1') and δ9.83ppm (t/3H/ω-methyl); molecular ion; m/e=370.

A solution of 1.5 g. of dl-3-(1',1'-dimethylheptyl)-6,6a,7,8-tetrahydro-1-hydroxy-6,6-dimethyl-9H-dibenzo[b,d]pyran-9-one in 50 ml. of anhydrous tetrahydrofuran (THF) was added dropwise to a solution of lithium metal in liquid ammonia at −80° C. Excess lithium metal was added in chunks to the solution as the blue color, indicating free dissolved lithium, disappeared. After the addition was complete, ammonium chloride was added to react with any excess lithium metal still present. The mixture was then allowed to warm to room temperature in a nitrogen atmosphere during which process the ammonia evaporated. The reaction mixture was then acidified with 1N aqueous hydrochloric acid, and the organic constituents extracted with ethyl acetate. The ethyl acetate extracts were combined, washed with water and dried. Evaporation of the ethyl acetate under reduced pressure yielded 1.4 g. of crude dl-trans-3-(1',1'-dimethylheptyl)-6,6a,7,8,10,10a-hexahydro-1-hydroxy-6,6-dimethyl-9H-dibenzo[b,d]pyran-9-one. The crude product was chromatographed over 50 g. of silica gel from benzene solution and the desired product was eluted in 20 ml. fractions with a benzene eluant containing 2 percent ethyl acetate. Fractions 200-240 contained 808 mg. of a white crystalline solid comprising purified dl-trans-3-(1',1'-dimethylheptyl)-6,6a,7,8,10,10a-hexahydro-1-hydroxy-6,6-dimethyl-9H-dibenzo[b,d]pyran-9-one. The purified compound melted at 159°-160° C. after recrystallization from an ethyl acetate-hexane solvent mixture. R$_f$= 0.45 (silica gel, 20% ethyl acetate:benzene). UV(ethanol) λmax 207/280mμ (ε=47,000/250); IR(CHCl$_3$) 5.85 μ(C=O); NMR (CDCl$_3$) δ7.75(s/1H/exchanges with D$_2$O), δ6.36/6.34 (2d/J=2 cps/2H/H$_2$ and H$_4$), δ4.15(d broad/J=14,3 cps/1H/H$_{10α}$), δ3.08–0.7 (multiplet/32H), especially δ1.47/1.13 (2s/each 3H/6α and 6β CH$_3$), δ1.21(s/6H/gemdimethyl at C-1') and δ0.83 ppm (t/3H/ω-methyl); molecular ion, m/e 372.

Anal. Calcd. for C$_{24}$H$_{36}$O$_3$: C, 77.38; H; 9.74; O; 12.88; Found: C, 77,59; H; 9.68; O; 12.99.

dl-cis-3-(1',1'-dimethylheptyl)-6,6a,7,8,10,10a-hexahydro-1-hydroxy-6,6-dimethyl-9H-dibenzo[b,d]pyran-9-one was prepared by further elution of the above chromatographic column with benzene containing 5 percent ethyl acetate. 140 mg of a white crystalline solid consisting of dl-cis-3-(1',1'-dimethylheptyl)-6,6a,7,8,10,10a-hexahydro-1-hydroxy-6,6-dimethyl-9H-dibenzo[b,d]pyran-9-one having the following physical and chemical characteristics: m.p. = 151°–153° C; R$_f$ 0.38(Silica Gel, 20% EtOAc-benzene); NMR (CDCl$_3$) δ6.98(s/1H/exchanges with D$_2$O), δ6.36(s broad/2H/H$_2$ and H$_4$), δ1.40, 1.35(2s/each 3H/6α and 6β CH$_3$), δ1.20(s/6H/gem dimethyl at C-1') and δ0.83 ppm (t/3H/ω-methyl); molecular ion, m/e 372.

Anal. Calcd. for C$_{24}$H$_{36}$O$_3$: C, 77.38; H; 9.74; O; 12.88; Found: C, 77.61; H; 10.00; O; 12.57.

Other compounds preparable by the above procedure include:

dl-trans-3-(1',2'-dimethylheptyl)-6,6a,7,8,10,10a-hexahydro-1-hydroxy-6,6-dimethyl-9H-dibenzo[b,d]pyran-9-one having the following physical and chemical characteristics: m.p. 119°–120° C; R$_f$=0.68 (silica gel, 20% ethyl acetate:benzene); UV(C$_2$H$_5$OH) λmax 208/280mμ (ε=48,400/800); IR (CHCl$_3$) 5.85μ (C=O); NMR (CDCl$_3$) δ6.30(brs/2H/aromatics); δ4.23(d broad/J=14.0, 3.0 cps/1H/H$_{10α}$); δ1.50/1.15(2s/each 3H/6α and 6β CH$_3$) and δ0.82 ppm(t/3Hω-methyl); molecular ion, m/e=372.

Anal. Calcd. for C$_{24}$H$_{36}$O$_3$: C, 77.38; H; 9.74; O; 12.88; Found: C, 77.67; H; 9.98; O; 13.00.

dl-trans-3-n-heptyl-6,6a,7,8,10,10a-hexahydro-1-hydroxy-6,6-dimethyl-9H-dibenzo[b,d]pyran-9-one having the following physical and chemical characteristics: m.p. 116°–117° C; R$_f$=0.38 (Silica gel, 20% ethyl acetate:benzene); UV(C$_2$H$_5$OH) λmax 208.280mμ (ε=12,000/600); IR (CHCl$_3$) 5.87 μ (C=O); NMR (CDCl$_3$) δ7.95(s/1H/exchanges with D$_2$O), δ6.30(s broad/2H/H$_2$ and H$_4$), δ4.22(broad d/J = 14.0, 3.0/1H/H$_{10α}$), δ1.30/1.12(2s/each 3H/6α and 6β CH$_3$) and δ0.87 ppm (t/3H/ω-methyl): molecular ion, m/e = 344.

Anal. Calcd. for C$_{22}$H$_{32}$O$_3$: C, 76.70; H; 9.36; O; 13.93; Found: C, 76.80; H; 9.12; O; 13.68.

dl-trans-1-hydroxy-3-(1'-methylheptyl)-6,6-dimethyl-6,6a,7,8,10,10a-hexahydro-9H-dibenzo[b,d]pyran-9-one with these characteristics: m.p. 137°–138° R$_f$0.36 (Silica gel, 20% ethyl acetate:benzene); UV (EtOH) 208/280 mμ (ε=48,800/400); IR(CHCl$_3$) 5.86 μ (C=O); NMR (CDCl$_3$) δ7.8(s/1H/exchanges with D$_2$O), δ6.32(2H/H$_2$ and H$_4$), δ4.20(d broad/J=14/3 cps/1H/H$_{10α}$), δ1.48/1.13(2 s/each 3H/6α and 6β CH$_3$), δ1.23(s/6H/gem dimethyl at C-1') and δ0.83ppm (t/3H/ω-methyl); high resolution mass spec confirms MW = 358 and empirical formula C$_{23}$H$_{34}$O$_3$.

Other compounds preparable by the above procedure and useful in the processes of this invention include:

dl-trans-1-hydroxy-3-(1',1'-dimethylpentyl)-6,6-dimethyl-6,6a,7,8,10,10a-hexahydro-9H-dibenzo[b,d]pyran-9-one dl-trans-1-hydroxy-3-(1',1'-dimethylpropyl)-6,6-dimethyl-6,6a,7,8,10,10a-hexahydro-9H-dibenzo[b,d]pyran-9-one dl-trans-1-hydroxy-3-(1',1'-dimethyloctyl)-6,6-dimethyl-6,6a,7,8,10,10a-hexahydro-9H-dibenzo[b,d]pyran-9-one The 1-acetoxy derivatives according to the Formula IV in which R''' is C$_1$–C$_4$ lower alkanoyl are prepared by reacting a compound in which R''' is hydrogen with a lower alkanoyl chloride or anhydride.

EXAMPLE 2

Preparation of dl-trans-1-acetoxy-3-(1',1'-dimethylheptyl)-6,6-dimethyl-6,6a,7,8,10,10a-hexahydro-9H-dibenzo[b,d]pyran-9-one:

A mixture of 500 mg. of dl-trans-1-hydroxy-3-(1',1'-dimethylheptyl)-6,6-dimethyl-6,6a,7,8,10,10a-hexahydro-9H-dibenzo[b,d]pyran-9-one, 5 ml. of acetic anhydride, and 5 ml. of pyridine was stirred under an inert atmosphere for 16 hours. The mixture was then poured onto ice and extracted with ethyl acetate. The ethyl acetate extract was washed with 1 N HCl and saturated sodium chloride solution, dried over anhydrous sodium sulfate and evaporated in vacuo to give 450 mg. of dl-trans-1-acetoxy-3-(1',1'-dimethylheptyl)-6,6-dimethyl-6,6a,7,8,10,10a-hexahydro-9H-dibenzo-[b,d]pyran-9-one as a viscous oil: R$_f$=0.33(Silica gel, 10% Ethyl acetate:benzene): IR (CHCl$_3$) 5.62, 5.80, and 8.28 μ; molecular ion at m/e 414. As previously mentioned, compounds represented by Formula IV above have the ability to produce bronchodilitation in humans and can alleviate bronchial asthma in man. Bronchial asthma, including both extrinsic or allergic asthma and intrinsic or infective asthma, is characterized by recurrent paroxysms of dyspnea associated with a characteristic type of wheezing caused by obstruction of the flow of air in the smaller bronchi and bronchioles. In more severe attacks, trapping of air in the alveoli may occur, completely obstructing the airways, which event may result in death. Drugs represented by Formula IV above appear to act to alleviate asthmatic symptoms by relaxing bronchial smooth muscle thereby increasing the passage of air from the lung. They may also act, in part, by a central mechanism relieving anxiety, a major component of this disease.

Other compounds within the scope of Formula IV above which are useful in the treatment of asthma include dl-trans-1-hydroxy-3-(1',2'-dimethylheptyl)-6,6-dimethyl-6,6a,7,8,10,10a-hexahydro-9H-dibenzo[b,d]pyran-9-one, dl-cis-1-hydroxy-3-(1',1'-dimethylheptyl)-6,6-dimethyl-6,6a,7,8,10,10a-hexahydro-9H-dibenzo[b,d]pyran-9-one, dl-trans-1-hydroxy-3-(1'-methylheptyl)-6,6-dimethyl-6,6a,7,8,10,10a-hexahydro-9H-dibenzo[b,d]pyran-9-one, dl-trans-1-hydroxy-3-(n-heptyl)-6,6-dimethyl-6,6a,7,8,10,10a-hexahydro-9H-dibenzo[b,d]pyran-9-one, dl-trans-1-hydroxy-3-(1',1'-dimethylpentyl)-6,6-dimethyl-6,6a,7,8,10,10a-hexahydro-9H-dibenzo[b,d]pyran-9-one, dl-trans-1-hydroxy-3-(1',1'-dimethylpropyl)-6,6-dimethyl-6,6a,7,8,10,10a-hexahydro-9H-dibenzo[b,d]pyran-9-one, dl-trans-1-hydroxy-3-(1',1'-dimethyloctyl)-6,6-dimethyl-6,6a,7,8,10,10a-hexahydro-9H-dibenzo[b,d]pyran-9-one, and dl-trans-1-acetoxy-3-(1',1'-dimethylheptyl)-6,6-dimethyl-6,6a,7,8,10,10a-hexahydro-9H-dibenzo[b,d]pyran-9-one.

Compounds represented by Formula IV above can be administered to mammals suffering from asthma by either the oral or parenteral route, the oral route being preferred. The compounds are relatively insoluble and in preparing any pharmaceutical form containing them it is desirable that the compound be in a finely divided state such as that obtainable after rapid evaporation of a solution of the drug. In addition, aqueous suspensions of the drug should be used as soon as possible after being prepared, and the suspension concentrate should be maintained in the dry state until use since it has been found that, upon standing in solution, the compound which was originally in a finely divided state may slowly crystallize to a less absorbable form. Preferably, a polymorphic form of the drug, prepared by rapidly adding an ethanolic solution thereof to a large quantity of water, as set forth in the copending application of Arvind L. Thakkar, Ser. No. 413,011. filed Nov. 5, 1973 now abandoned, and in continuation-in-part application of Thakkar Ser. No. 504,391 filed Sept. 11, 1974, now abandoned, in continuation-in-part application Ser. No. 628,251, filed Dec. 8, 1975, of Thakkar, now abandoned and in continuation-in-part application of Thakkar, Ser. No. 707,786 filed July 22, 1976 should be used. The polymorphic form thus prepared is stable and readily absorbable, giving satisfactory drug blood levels after oral administration. It does not revert (probably by recrystallization) to less absorbable crystalline forms on standing for periods of time up to two weeks or longer.

An aqueous suspension of a drug represented by Formula IV for use as an antiasthmatic is prepared as follows: An acetone solution containing 2 parts of weight of, for example 1-hydroxy-3-(1',1'-dimethylheptyl)-6,6-dimethyl-6,6a,7,8,10,10a-hexahydro-9H-dibenzo[b,d]-pyran-9-one is mixed with 1 part by weight of aqueous polyoxyethylenesorbitan monooleate. The solution is placed in a glass ampoule and the acetone evaporated in vacuo. Just before use, 100 parts by weight of water are added giving a final concentration of 2 mg/ml. An intravenous formulation useful in severe asthma attacks can be prepared by dissolving 1 mg. of dl-trans-1-hydroxy-3-(1',1'-dimethylheptyl)-6,6-dimethyl-6,6a,7,8,10,10a-hexahydro-9H-dibenzo[b,d]pyran-9-one or other active drug represented by Formula IV in 1 ml. of absolute alcohol and dilute to 100 ml. volume with an isotonic solution.

Capsules containing a drug according to formula IV above suitable for use in the processes of this invention can be prepared as follows: 1 part of weight of drug (obtained by adding an ethanol solution thereof rapidly to a large volume of water and then collecting the precipitate) is mixed with 9 parts of starch and the mixture loaded into empty telescoping gelatin capsules such that each capsules contains 10 mg of drug and 90 mg. of starch. Alternatively, a mixture containing 10 parts of drug from acetone solution, 1 part of polyoxyethylenesorbitan monooleate or similar suitable surfactant and 89 parts of starch are thoroughly mixed and placed in empty telescoping gelatin capsules such that each capsule will contain 10 mg. of drug. Solutions of compounds according to the above formula for use in oral administration can be prepared in any desired strength in polyethyleneglycol 300 (N.F.). In addition, drugs according to Formula IV above in absorbable polymorphic form can be compounded into scored tablets containing from 0.4 to 100 mg of drug per tablet, along with other standard ingredients used in preparing tablets such as starch, a lubricants and binders.

One preferred mode of administration of a dibenzo[b,d]pyran-9-one according to Formula IV above is in the form of a dispersion with polyvinylpyrrolidone as taught in the copending application of Arvind L. Thakkar, Ser. No. 413,012, filed Nov. 5, 1973 now U.S. Pat. No. 3,920,809 issued Nov. 18, 1975. In accordance with the teachings of Thakkar, a polyvinylpyrrolidone (PVP) complex is formed with the active drug having a structure of Formula IV above, for example 1-hydroxy-3-(1',1'-dimethylheptyl)-6,6-dimethyl-6,6a,7,8,10,10a-hexahydro-9H-dibenzo[b,d]pyran-9-one. In preparing the complex, a solution of 90 parts of PVP dissolved in ethanol is mixed with an ethanol solution containing 10 parts of drug, and the ethanol is evaporated therefrom in vacuo. The resulting solid is then mixed with 89 parts of starch and 1 part of polyoxyethylenesorbitan monooleate, and the mixture loaded into an empty telescoping gelatin capsules such that each capsule contains 5 mg. of drug.

As will be understood by those versed in the art, it is possible to vary the amount of drug in each of the above dosage forms so that unit dosage will contain from 0.1 to 25 mg. of drug with final daily dosages of from 0.1 to 100 mg/patient.

In treating mammals suffering from asthma daily dosages of from 0.1 to 100 mg of active drug according to formula IV above are customarily administered.

We claim:

1. A process for providing relief from asthma in mammals which comprises administering to a mammal suffering from asthma an antiasthmatic dose of a compound represented by the formula

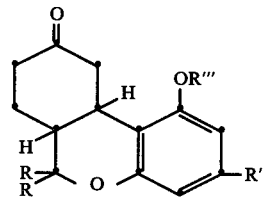

wherein R' is either $C_7$–$C_{10}$ normal alkyl or is the group

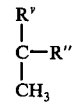

wherein R" is $C_2$–$C_7$ alkyl and R$^v$ is H or methyl, wherein both R groups are identical and are H or methyl and wherein R'" is H or $C_1$–$C_4$ alkanoyl, in an amount effective to relieve asthma.

2. A process according to claim 1 in which a dose of from 0.1 to 100 mgs per day of the drug is administered.

3. A process according to claim 1 in which a dose of from 1 to 20 mgs. per day of the drug is administered.

4. A process according to claim 1 in which the drug is administered by the oral route.

5. A process according to claim 1 in which dl-trans-1-hydroxy-3-(1',1'-dimethylheptyl)-6,6a,7,8,10,10a-hexahydro-6,6-dimethyl-9H-dibenzo[b,d]pyran-9-one is administered.

6. A process according to claim 1 in which dl-trans-1-hydroxy-3-(1',2'-dimethylheptyl)-6,6a,7,8,10,10a-hexahydro-6,6-dimethyl-9H-dibenzo[b,d]pyran-9-one is administered.

7. A process according to claim 1 in which dl-trans-1-hydroxy-3-(1'-methylheptyl)-6,6a,7,8,10,10a-hexahydro-6,6-dimethyl-9H-dibenzo[b,d]pyran-9-one is administered.

* * * * *